(12) United States Patent
Weigand

(10) Patent No.: US 11,383,101 B2
(45) Date of Patent: Jul. 12, 2022

(54) APPLICATOR, APPLICATOR SYSTEM AND METHOD FOR USING AN APPLICATOR WITH A RADIOTHERAPY DEVICE

(71) Applicant: Carl Zeiss Meditec AG, Jena (DE)

(72) Inventor: Frank Weigand, Heidenheim (DE)

(73) Assignee: Carl Zeiss Meditec AG, Jena (DE)

(*) Notice: Subject to any disclaimer, the term of this patent is extended or adjusted under 35 U.S.C. 154(b) by 0 days.

(21) Appl. No.: 17/033,828

(22) Filed: Sep. 27, 2020

(65) Prior Publication Data

US 2021/0093889 A1    Apr. 1, 2021

(30) Foreign Application Priority Data

Sep. 27, 2019 (DE) ..................... 10 2019 126 127.9

(51) Int. Cl.
  *A61N 5/10*       (2006.01)
(52) U.S. Cl.
  CPC .... *A61N 5/1007* (2013.01); *A61N 2005/1008* (2013.01); *A61N 2005/1019* (2013.01); *A61N 2005/1098* (2013.01)
(58) Field of Classification Search
  CPC ...... A61N 5/10; A61N 5/1001; A61N 5/1007; A61N 5/1014; A61N 5/1015; A61N 5/1016; A61N 5/1017; A61N 5/1028; A61N 2005/1008; A61N 2005/1019; A61N 2005/1024
  See application file for complete search history.

(56) References Cited

U.S. PATENT DOCUMENTS

| | | | |
|---|---|---|---|
| 2,559,793 A * | 7/1951 | Pregel | G21G 4/06 600/1 |
| 6,285,735 B1 | 9/2001 | Sliski et al. | |
| 6,421,416 B1 | 7/2002 | Sliski et al. | |
| 7,109,505 B1 * | 9/2006 | Sliski | A61N 5/1001 250/505.1 |
| 2002/0022758 A1 | 2/2002 | Wolfson et al. | |
| 2009/0227827 A1 * | 9/2009 | Hausen | A61N 5/1016 600/6 |

(Continued)

FOREIGN PATENT DOCUMENTS

| | | |
|---|---|---|
| DE | 60109437 T2 | 4/2006 |
| DE | 102012002466 A1 | 8/2013 |

(Continued)

OTHER PUBLICATIONS

German Office Action, with translation thereof, for corresponding DE application No. 10 2019 126 127.9 dated May 5, 2020.

(Continued)

*Primary Examiner* — Samuel G Gilbert
(74) *Attorney, Agent, or Firm* — Falk Ewers; Ewers IP Law PLLC

(57) ABSTRACT

The present disclosure lies in the field of medical radiotherapy and relates to an applicator for a medical radiotherapy device, an applicator system for a medical radiotherapy device and a method for using an applicator or an applicator system. The applicator includes an applicator head and an applicator body. The applicator head and the applicator body are embodied such that the applicator head can be assembled on, and disassembled from, the applicator body, in each case without damage.

19 Claims, 5 Drawing Sheets

(56) References Cited

U.S. PATENT DOCUMENTS

| | | |
|---|---|---|
| 2011/0216885 A1 | 9/2011 | Kleinwaechter et al. |
| 2011/0257459 A1 | 10/2011 | Sutton et al. |
| 2014/0121443 A1 | 5/2014 | van Erp et al. |
| 2014/0206925 A1 | 7/2014 | Gerard et al. |
| 2014/0288350 A1 | 9/2014 | Kleinwaechter et al. |

FOREIGN PATENT DOCUMENTS

| | | |
|---|---|---|
| DE | 112013005144 T5 | 7/2015 |
| EP | 2335777 A2 | 6/2011 |
| JP | 2016032595 A | 3/2016 |
| WO | 0158346 A1 | 8/2001 |

OTHER PUBLICATIONS

Extended European Search Report dated Mar. 1, 2021 of European counterpart application No. EP 20198335.0 and English language translation thereof.

Varian: "Varian Brachytherapy Applicators and Accessories", Jan. 1, 2011, XP055339041, found on the Internet: URL:https://www.varian com/sites/default/files/resource_attachments/Brachytherapy_Applicators_Accessories_Catalogue_0_0.pdf.

Office Action issued in German Patent Application No. DE 10 2019 126 127.9 (from which this application claims priority), dated Nov. 30, 2021 and English language translation thereof.

* cited by examiner

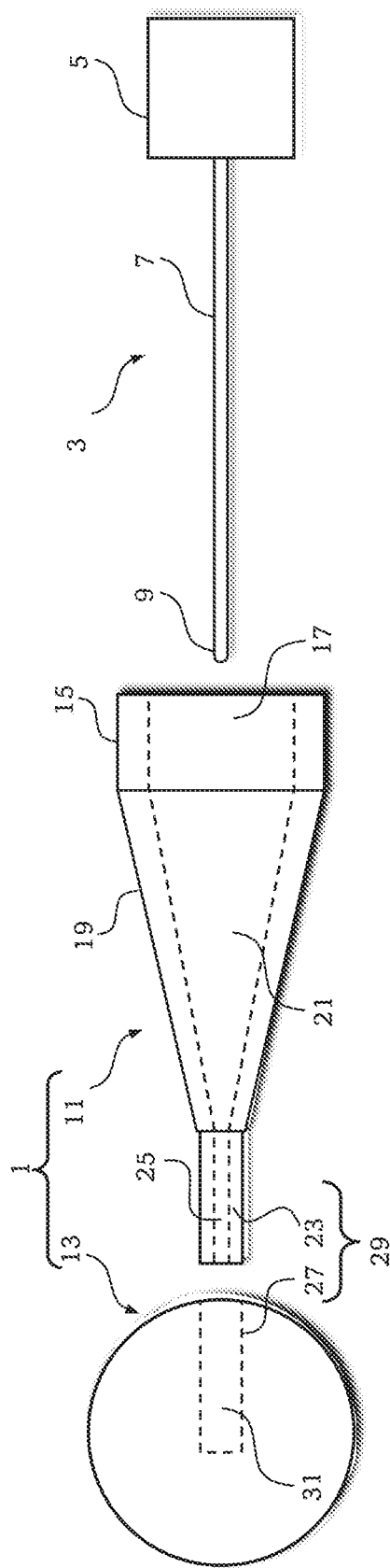
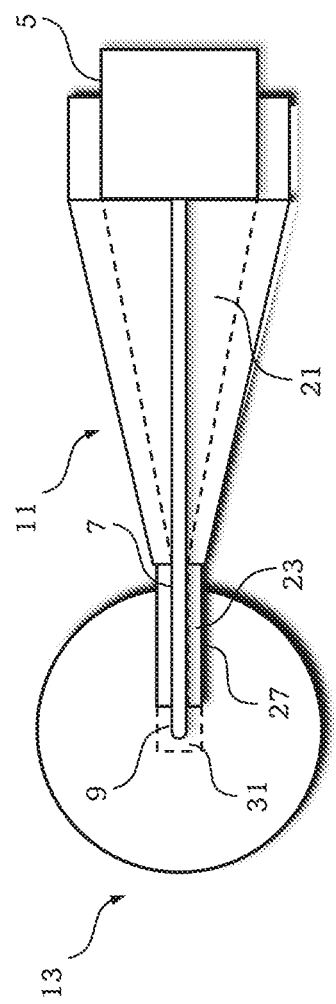
FIG. 1A
FIG. 1B

APPLICATOR, APPLICATOR SYSTEM AND METHOD FOR USING AN APPLICATOR WITH A RADIOTHERAPY DEVICE

CROSS REFERENCE TO RELATED APPLICATIONS

This application claims priority to German patent application DE 10 2019 126 127.9, filed Sep. 27, 2019, the entire content of which is incorporated herein by reference.

TECHNICAL FIELD

The present disclosure lies in the field of medical radiotherapy and relates to an applicator for a medical radiotherapy device, an applicator system for a medical radiotherapy device and a method for using an applicator or an applicator system.

BACKGROUND

There are medical radiotherapy devices for local irradiation of a body, to be treated by therapy, with radiation, in particular x-ray radiation. In the field of therapy using x-ray radiation, there are therapies in which x-ray radiation should be generated in the interior of a human or animal body, in the vicinity of tissue to be treated by therapy.

An exemplary radiotherapy device includes a particle beam system, which can generate a high energy particle beam. The particle beam is directed through a tube of the radiotherapy device, a few centimeters in length, at an x-ray material arranged at the end of said tube. As a result of interaction between the particle beam and the x-ray material, the latter generates x-ray radiation which is provided for treating tissue by therapy.

The tube is inserted into the body so that the x-ray radiation generated by the x-ray material at the tip of the tube can be applied in the interior of a body. To this end, the tube is surrounded by an applicator that can be placed on the radiotherapy device, said applicator firstly representing a sterile barrier and secondly protecting the tube of the radiotherapy device.

Such applicators must be produced from a material that has been approved for medical applications (e.g., Ultem®). Conventionally, an applicator is embodied as a single piece, for example by virtue of the final shape of the applicator being milled from a blank. As a rule, the material removed from the blank by milling cannot be reused. Accordingly, the production of an applicator is complicated, since very precise machine processing is required, and expensive, since a large proportion of the blank is discarded.

As a rule, a plurality of different applicators of different shapes and sizes are required for the treatment by therapy with x-ray radiation. Procuring a suitable set of applicators is therefore expensive, especially if the applicators have a single-piece embodiment.

SUMMARY

Accordingly, there is a need for a set of applicators that can be produced more easily and more cost-effectively. Accordingly, it is an object of the present disclosure to provide a set of applicators, which can be produced more easily and cost-effectively, and which can be used more flexibly.

This object is achieved by an applicator for a medical radiotherapy device for treatment by therapy with radiation. The applicator includes an applicator head and an applicator body. The applicator head and the applicator body are embodied in such a way that the applicator head can be assembled on, and disassembled from, the applicator body, in each case without damage.

Further, the object is achieved by an applicator system including a plurality of different such applicators, wherein the applicator body of all applicators is the same. The applicators of the applicator system can have different sizes and/or shapes when the respective applicator heads are assembled on the applicator body.

Further, the object is achieved by a method including: providing such an applicator, wherein the applicator head is assembled on the applicator body, following the provision, disassembling the applicator head from the applicator body without damage, and, following disassembly, assembling the applicator head or another applicator head on the applicator body.

The applicator according to an aspect of the disclosure is distinguished in that the applicator head can be assembled on, and disassembled from, the applicator body, in each case without damage. Therefore, one and the same applicator body can be used with various applicator heads. That is to say, different applicator heads can be assembled on, and disassembled from, the same applicator body, in each case without damage. A set of various applicators, which is also referred to as applicator system herein, can therefore easily be provided by a single applicator body and various applicator heads since the various applicator heads can be assembled on, and disassembled from, one and the same applicator body, in each case without damage.

By way of example, assembly and disassembly, in each case without damage, means that the applicator head and the applicator body have the same physical form in the assembled and disassembled state respectively. By way of example, this means that neither the shape of the applicator head nor the shape of the applicator body is altered by assembly and disassembly.

Assembly and disassembly, in each case without damage, can moreover or alternatively mean that the applicator head and the applicator body can be assembled on, and disassembled from, one another without additional objects (e.g., adhesives).

Examples of a mechanical connection between the applicator head and the applicator body, which can be closed (assembly without damage) and released (disassembly without damage), in each case without damage, include plug connections, screw connections, force-fit connections, interlocking connections and the like. Examples of mechanical connections which cannot be established and released without damage include material connections, such as adhesive connections.

The applicator can be made from a material that has been approved for the medical purposes. By way of example, Ultem® is such a material. The individual components of an applicator can be made from the same material. In particular, the applicator head and the applicator body can be made from the same material. In particular, applicator head elements of the applicator head and the applicator body can be made from the same material. The applicator head can include a plurality of applicator head elements, which have a different absorption characteristic in respect of the radiation used by the radiotherapy device.

BRIEF DESCRIPTION OF THE DRAWINGS

The disclosure will now be described with reference to the drawings wherein:

FIG. 1A shows a schematic illustration of a cross section of a radiotherapy device and of an applicator in a disassembled state according to an exemplary embodiment of the disclosure, FIG. 1B shows a schematic illustration of a cross section of the applicator shown in FIG. 1A in an assembled state, wherein the radiotherapy device is inserted into the applicator.

DESCRIPTION OF EXEMPLARY EMBODIMENTS

Figure 2A:
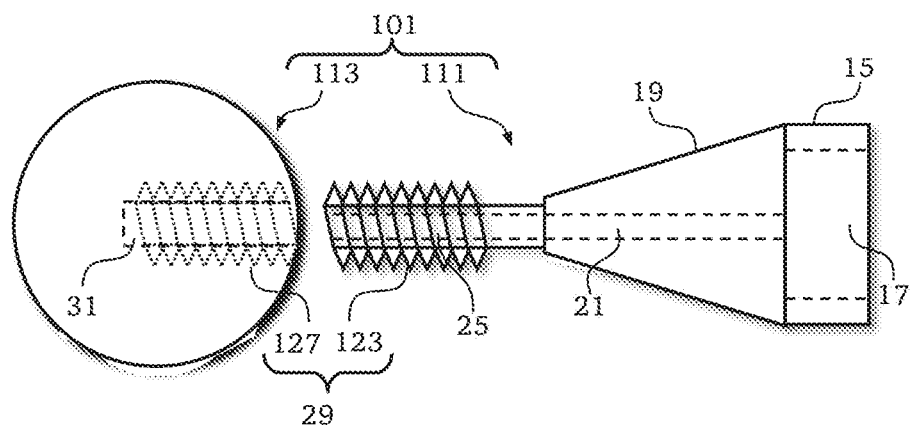
FIG. 2A shows a schematic illustration of a cross section of an applicator in a disassembled state according to a further exemplary embodiment of the disclosure.

Below, a first exemplary embodiment of an applicator 1 for a medical radiotherapy device 3 is described with reference to FIGS. 1A and 1B. FIG. 1A shows a schematic illustration of a cross section through the applicator 1 and the radiotherapy device 3, with the applicator 1 being illustrated in a disassembled state, i.e., in a state in which an applicator head 13 of the applicator 1 is not assembled on an applicator body 11 of the applicator 1 and the radiotherapy device 3 is not inserted into the applicator 1. FIG. 1B shows a schematic illustration of a cross section through the applicator 1 and the radiotherapy device 3, with the applicator 1 being illustrated in an assembled state, i.e., in a state in which the applicator head 13 is assembled on the applicator body 11 and the radiotherapy device 3 is inserted into the applicator 1.

The radiotherapy device 3 includes a main body 5 with a tube 7 extending away from the main body 5. An x-ray material suitable for emitting x-ray radiation can be arranged (in the interior of the tube 7) at an end 9 of the tube 7 distant from the main body 5.

The radiotherapy device 3 is configured to generate the x-ray radiation with the x-ray material. To this end, the radiotherapy device 3 can include a particle beam system not shown in the figures, which is arranged in the interior of the main body 5 and which directs a particle beam in the interior of the tube 7 at the x-ray material, the latter emitting the x-ray radiation as a result of the interaction with the particle beam.

The applicator 1 includes an applicator body 11 and an applicator head 13. The applicator body 11 and the applicator head 13 are separate parts, each of which have a single-piece embodiment.

The applicator body 11 includes an adapter section 15, which is configured to be connected to the radiotherapy device 3. In particular, the adapter section 15 is configured to be connected to the main body 5 of the radiotherapy device 3. In the exemplary embodiment shown in FIG. 1A, the adapter section 15 is a substantially tubular section with an interior 17, in which the main body 5 of the radiotherapy device 3 can be arranged at least in part.

The applicator body 11 further includes a mid section 19, which adjoins the adapter section 15. The mid section 19 has a conically tapering tubular shape. The mid section 19 surrounds an interior 21, which is connected to the interior 17 of the adapter section 15.

The applicator body 11 further includes a connecting section 23. The connecting section 23 has a substantially tubular shape. An interior 25 surrounded by the connecting section 23 adjoins the interior 21 of the mid section 19. The connecting section 23 serves to connect (assemble) the applicator body 11 to (on) the applicator head 13.

In the exemplary embodiment shown in FIG. 1A, the applicator head 13 has a substantially spherical external shape. However, the external shape of the applicator head 13 could be any other desired external shape, for example an ellipsoid shape. The shape of the applicator head is selected on the basis of the body to be treated by therapy. In the case of a therapy application (irradiation), the applicator 1 is introduced into the body to be treated by therapy such that at least part of the applicator head 13 is inserted into the body to be treated by therapy. Here, the surface of the applicator head 13 supports the tissue to be treated by therapy and moreover serves to generate a desired radiation profile.

The applicator head 13 includes a connecting section 27. In the exemplary embodiment shown in FIG. 1A, the connecting section 27 of the applicator head 13 is a cylindrical cutout in the interior of the applicator head 13, which extends up to the surface.

The applicator head 13 further includes an interior 31, in which the end 9 of the radiotherapy device 3 is arranged when the applicator head 13 is assembled on the applicator body 11. In the exemplary embodiment shown in FIGS. 1A and 1B, the cutout providing the connecting section 27 is part of the interior 31.

The connecting section 23 of the applicator body 11 and the connecting section 27 of the applicator head 13 together form a first assembling mechanism 29, which is configured to provide a mechanical connection between applicator head 13 and applicator body 11, which can be released without damage. In the exemplary embodiment shown in FIG. 1A, the first assembling mechanism 29 provides a plug connection, which can be formed by the connecting sections 23 and 27. This means that the applicator head 13 can be assembled on the applicator body 11 (can be mechanically connected to the latter) by virtue of the connecting section 23 being inserted into the connecting section 27, wherein a frictional connection forms a force-fit connection between the applicator head 13 and the applicator body 11. This mechanical connection can be released without damage by virtue of the applicator head 13 being pulled off the applicator body 11.

In FIG. 1B, the applicator head 13 is assembled on the applicator body 11. Assembly is implemented with the above-described plug connection by way of the connecting sections 23 and 27. Consequently, the applicator 1 is in an assembled state.

Moreover, the radiotherapy device 3 is inserted in the assembled applicator 1. The main body 5 of the radiotherapy device 3 is partly situated in the interior 17 of the adapter section 15 of the applicator body 11 in this case. Further, the tube 7 of the radiotherapy device 3 passes through the interiors 21 and 25 of the applicator 1 and emerges from the applicator 1 at a front end of the connecting section 23. The end 9 of the radiotherapy device 3 is situated in the interior 31. Consequently, the end 9 of the radiotherapy device 3 is approximately in the center of the applicator head 13.

The first assembling mechanism 29 is embodied such that it can provide a mechanical connection between applicator head 13 and applicator body 11, which can be released without damage. As shown in the example of FIG. 1A, the connecting sections 23 and 27, which form the first assembling mechanism 29, are embodied as sections of the applicator head 13 and of the applicator body 11. Therefore, the applicator head 13 and the applicator body 11 are embodied in such a way that the applicator head 13 can be assembled on, and disassembled from, the applicator body 11, in each case without damage.

This configuration of the applicator 1 allows the use of a plurality of different applicator heads with one and the same applicator body 11. A set of applicators, also referred to as applicator system, can therefore be provided by one applicator body and a plurality of (different) applicator heads, wherein each of the applicator heads can individually be assembled on, and disassembled from, the applicator body, in each case without damage.

Figure 2B:
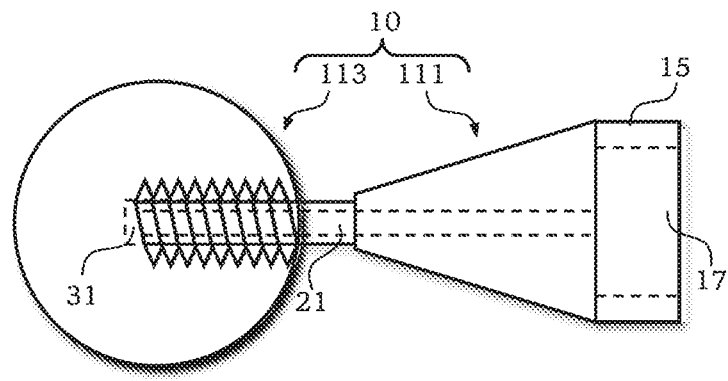
FIG. 2B shows a schematic illustration of a cross section of the applicator shown in FIG. 2A in an assembled state.

A second exemplary embodiment of an applicator 101 is described below with reference to FIGS. 2A and 2B, wherein FIG. 2A shows a schematic illustration of a cross section through the applicator 101 in a disassembled state while FIG. 2B shows a schematic illustration of a cross section through the applicator 101 in an assembled state.

The applicator 101 includes an applicator body 111 and an applicator head 113. The applicator body 111 substantially only differs from the applicator body 11 shown in FIG. 1A by the specific configuration of the connecting section. Accordingly, only the differences to the applicator body 11 shown in FIG. 1A are described. For the components provided with the same reference sign, the description in respect of FIG. 1A applies. The applicator body 111 includes a connecting section 123, which is formed by a male thread in the exemplary embodiment shown in FIG. 2A.

Further, the applicator 101 includes the applicator head 113, the external shape of which corresponds to that of the applicator head 13 in FIG. 1A. The applicator head 113 includes a connecting section 127, which is a female thread in the exemplary embodiment shown in FIG. 2A and which fits to the connecting section 123 (male thread) of the applicator body 111. The connecting section 127 is located within the substantially spherical surface of the applicator head 113. Together, the connecting sections 123 and 127 form the first assembling mechanism 29.

The applicator head 113 can be assembled on the applicator body 111 without damage by virtue of the connecting sections 123 and 127 been screwed into one another, as illustrated in FIG. 2B. The applicator head 113 can be disassembled from the applicator body 111 without damage by virtue of the applicator head 113 being screwed off the applicator body 111, as shown in FIG. 2A. In the exemplary embodiment shown in FIGS. 2A and 2B, the first assembling mechanism 29 is a screw connection.

The same effects can be obtained with the applicator 101 shown in FIGS. 2A and 2B as with the applicator 1 shown in FIGS. 1A and 1B.

Figure 3A:
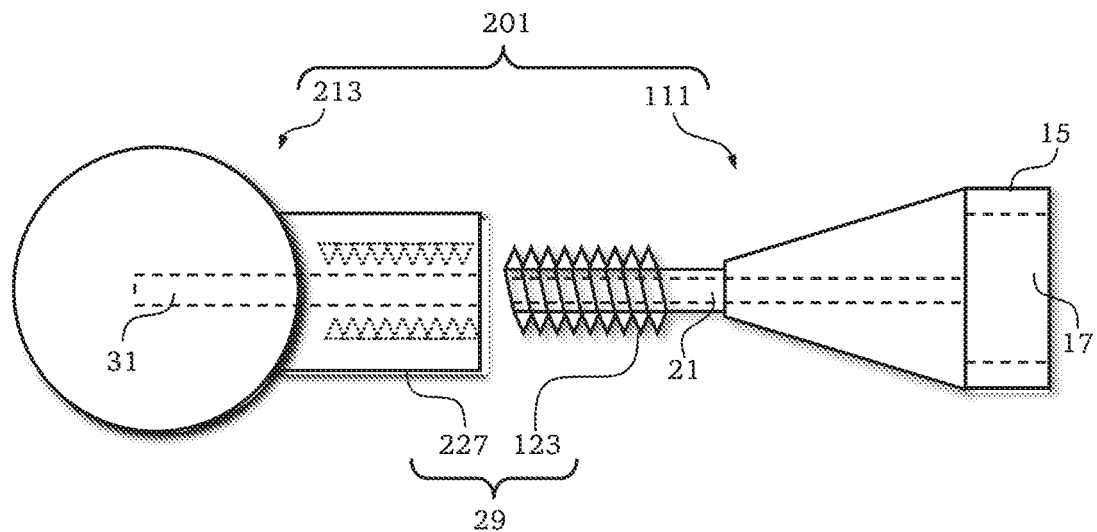
FIG. 3A shows a schematic illustration of a cross section of an applicator in a disassembled state according to a further exemplary embodiment of the disclosure.
Figure 3B:
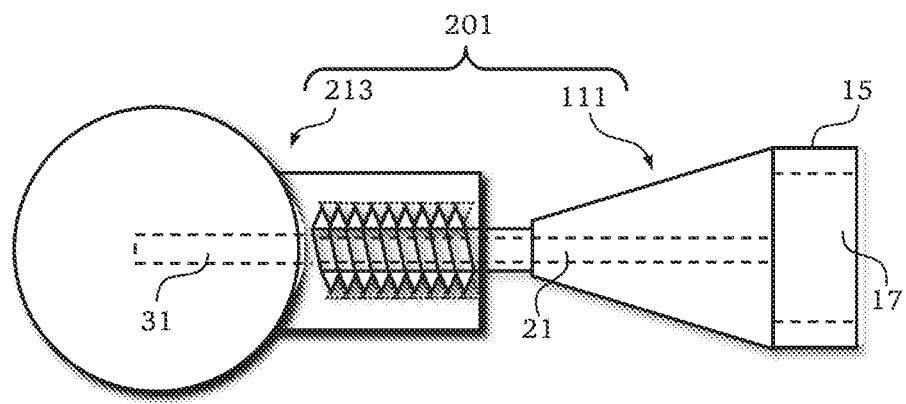
FIG. 3B shows a schematic illustration of a cross section of the applicator shown in FIG. 3A in an assembled state.

A third exemplary embodiment of an applicator 201 is described below with reference to FIGS. 3A and 3B, wherein FIG. 3A shows a schematic illustration of a cross section through the applicator 201 in a disassembled state while FIG. 3B shows a schematic illustration of a cross section through the applicator 201 in an assembled state.

The applicator 201 includes the applicator body 111 and an applicator head 213. The applicator body 111 corresponds to the applicator body described in conjunction with the applicator 101.

The external shape of the applicator head 213 corresponds to that of the applicator head 13 in FIG. 1A. The applicator head 213 includes a connecting section 227, which is a female thread in the exemplary embodiment shown in FIG. 3A and which fits to the connecting section 123 (male thread) of the applicator body 111. The connecting section 227 is located outside of the substantially spherical surface of the applicator head 213. Together, the connecting sections 123 and 227 form the first assembling mechanism 29.

The applicator head 213 can be assembled on the applicator body 111 without damage by virtue of the connecting sections 123 and 227 been screwed into one another, as illustrated in FIG. 3B. The applicator head 213 can be disassembled from the applicator body 111 without damage by virtue of the applicator head 213 being screwed off the applicator body 111, as shown in FIG. 3A. In the exemplary embodiment shown in FIGS. 3A and 3B, the first assembling mechanism 29 is a screw connection.

The same effects can be obtained with the applicator 201 shown in FIGS. 3A and 3B as with the applicators 1 and 101 shown in FIGS. 1A, 1B, 2A, and 2B.

A fourth exemplary embodiment of an applicator 301 is described below with reference to FIGS. 4A to 4C.

Figure 4A:
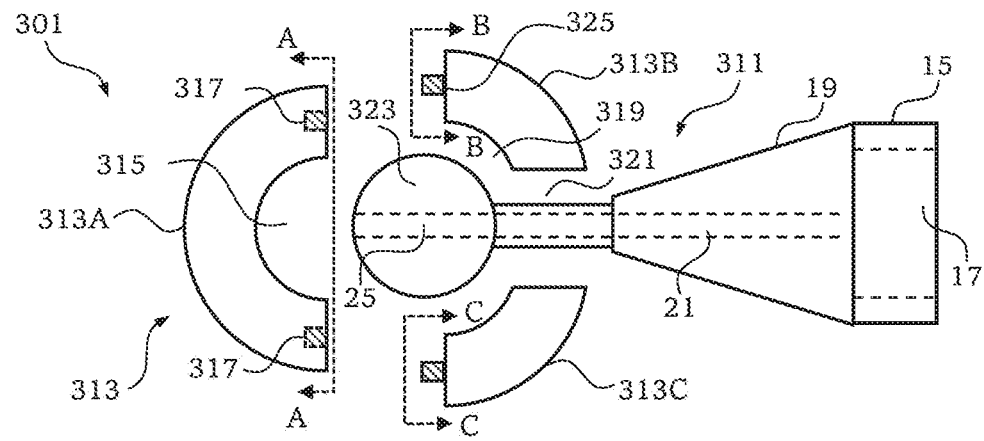
FIG. 4A shows a schematic illustration of a cross section of an applicator in a disassembled state according to a further exemplary embodiment of the disclosure.

FIG. 4A shows a schematic illustration of a cross section through the applicator 301 in a disassembled state. FIG. 4B shows a schematic illustration of a cross section of applicator head elements of the applicator 301 shown in FIG. 4A, in a disassembled state, wherein the cross section of FIG. 4B is oriented perpendicular to the cross section of FIGS. 4A and 4C. FIG. 4C shows a schematic illustration of a cross section through the applicator 301, shown in FIG. 4A, in an assembled state.

The applicator 301 includes an applicator body 311 and an applicator head 313.

The applicator body 311 substantially only differs from the applicator body 11 shown in FIG. 1A in that the connecting section 323 of the applicator body 311 has a substantially spherical external shape.

The applicator head 313 includes a plurality of applicator head elements. In the exemplary embodiment shown in FIGS. 4A to 4C, the applicator head 313 includes three separate applicator head elements 313A, 313B, and 313C. FIG. 4B shows an illustration of the applicator head element 313A along the cross-section A-A, which is oriented perpendicular to the plane of the drawing of FIG. 4A, along the direction of the arrow, i.e., to the left in FIG. 4A. FIG. 4B further shows an illustration of the applicator head element 313B along the cross-section B-B, which is oriented perpendicular to the plane of the drawing of FIG. 4A, along the direction of the arrow, i.e., to the right in FIG. 4A. FIG. 4B further shows an illustration of the applicator head element 313C along the cross-section C-C, which is oriented perpendicular to the plane of the drawing of FIG. 4A, along the direction of the arrow, i.e., to the right in FIG. 4A.

The applicator head element 313 has a substantially hemispherical external shape with a hemispherical cutout 315, which corresponds to the size of the connecting section 323 of the applicator body 311. The applicator head element 313A further has a female thread 317.

The applicator head element 313B has a substantially spherical segment-shaped external shape and moreover has two cutouts 319 and 321. The cutout 319 is a spherical segment-shaped cutout, the shape and size of which is matched to the size of the connecting section 323 of the applicator body 311. The cutout 321 is a cylindrical cutout, the shape and size of which is matched to that of the mid-section 19 of the applicator body element 311. The applicator head element 313B further includes a male thread 325. The male thread 325 is matched to the female thread 317.

The applicator head element 313C substantially corresponds to the applicator head element 313B, wherein the male thread 325 of the applicator head element 313C and the male thread 325 of the applicator head element 313B are matched to one another in such a way that a functionally interacting male thread arises therefrom, which can be screwed into the female thread 317 of the applicator head element when a side 326B of the applicator head element 313B (see FIG. 4B) and a side 326C of the applicator head element 313C are placed against one another.

The applicator head elements 313A, 313B, and 313C are embodied in such a way that they can be assembled on, and disassembled from, one another, in each case without damage. In the exemplary embodiment shown in FIGS. 4A to 4C, the female thread 317 and the male thread made from the functionally interacting male threads 325 of the applicator head elements 313B and 313C provide a second assembling mechanism, which is configured to provide a mechanical connection between the applicator head elements 313A to 313C, which can be released without damage. By way of example, the applicator head elements 313A to 313C are assembled on one another without damage by virtue of the applicator head elements 313B and 313C being placed against one another at the sides 326B and 326C in order to form the functionally interacting male thread, which is subsequently screwed into the female thread 317 provided on the applicator head element 313A. Such a situation, in which the applicator head elements 313A to 313C are assembled on one another, is shown in FIG. 4C.

The applicator head 313 can be assembled on the applicator body 311 without damage as follows: The applicator head element 313A is placed on the connecting section 323 of the applicator body 311, with the connecting section 323 being inserted into the cutout 315 of the applicator head element 313A. The applicator head element 313B and the applicator head element 313C are placed against one another at the sides 326B and 326C, with the mid section 19 of the applicator body 311 passing through the cutout 321. Here, the applicator head element 313A and the applicator head elements 313B and 313C, the latter two placed against one another, are spaced apart along a longitudinal direction of the applicator (in the direction from left to right in FIG. 4A) so that the male threads 325 do not collide with the applicator head element 313A when the applicator head elements 313B and 313C are placed against one another. In this state, the connecting section 323 can already be partly inserted into the cutouts 319. Subsequently, the applicator head element 313A and the applicator head elements 313B and 313C, the latter two placed against one another, are pushed against one another along the longitudinal direction. Subsequently, the applicator head elements 313B and 313C, which are placed against one another, are screwed to the applicator head element 313A by virtue of the placed-together applicator head elements 313B and 313C being rotated relative to the applicator head element 313A about the longitudinal axis, as a result of which the female thread 317 and the functionally interacting male thread engage with one another.

The applicator head elements 313A to 313C can be disassembled from one another without damage by virtue of the screw connection being released, as is shown in FIG. 4A.

Figure 4B:
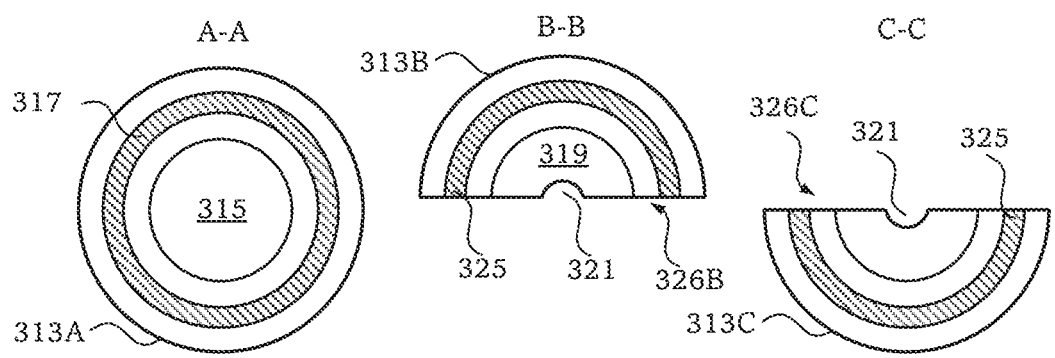
FIG. 4B shows a schematic illustration of a cross section of applicator head elements of the applicator shown in FIG. 4A, in a disassembled state, wherein the cross section of FIG. 4B is oriented perpendicular to the cross section shown in FIGS. 4A and 4C.
Figure 4C:
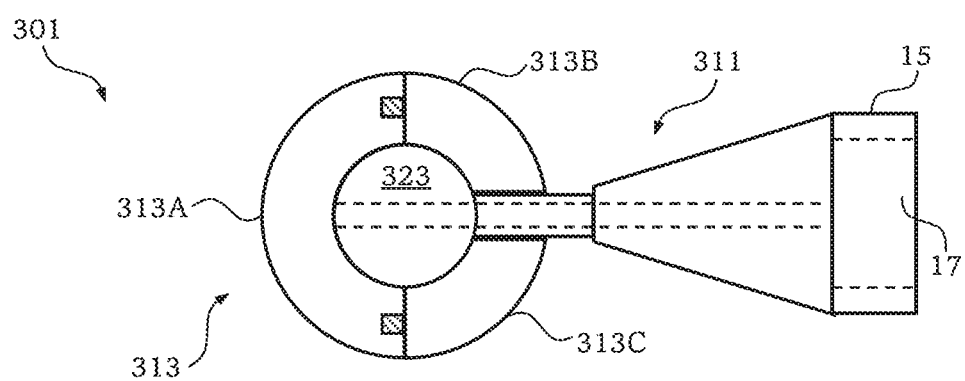
FIG. 4C shows a schematic illustration of a cross section of the applicator shown in FIG. 4A in an assembled state.

FIGS. 4A to 4C show an exemplary embodiment of the second assembling mechanism in the form of a screw connection. However, the second assembling mechanism can also be provided by another type of connection, in particular in the form of a plug connection, a force-fit connection or an interlocking connection.

In the exemplary embodiment shown in FIGS. 4A to 4C, the cutout 315 of the applicator head element 313A and the cutout 319 of the applicator head elements 313B and 313C are embodied such that the connecting section 323 of the applicator body 311 can be surrounded at least in part, in particular substantially completely and flush, by the applicator head elements 313A to 313C. As a result, the emission characteristic of the applicator head 313 substantially corresponds to the emission characteristic of an applicator head that is made of a single piece and has the same external form.

Expressed differently, the applicator head elements 313A to 313C can be arranged around the connecting section 323 and can be subsequently interconnected (with the second assembling mechanism), as illustrated in FIG. 4C. In the state where they are assembled on one another, the applicator head elements 313A to 313C form a spherical shell with suitable cutouts for the connecting section 323 and the mid section 19 of the applicator body 311. When the applicator head elements 313A to 313C are assembled on one another in this manner and, in the process, arranged around the connecting section 323, as shown in FIG. 4C, an interlocking connection between the applicator head 313 formed from the applicator head elements 313A to 313C and the applicator body 311 arises as a result thereof. This interlocking connection is an example of the first assembling mechanism 29. In this way, a mechanical connection between applicator head 313 and applicator body 311, which can be released without damage, is moreover formed by way of the mechanical connection between the applicator head elements 313A to 313C provided by the second assembling mechanism.

The connecting section 323 has a substantially spherical external shape in the example of FIG. 4A to 4C. Other external shapes are possible, in particular a substantially ellipsoid external shape.

In the exemplary embodiment shown in FIGS. 4A to 4C, the applicator head 313, which is formed by the applicator head elements 313A to 313C assembled on one another, has a substantially spherical external shape. Other external shapes are possible, in particular a substantially ellipsoid external shape.

The individual shapes of the components of the applicators described above are not restricted to the shapes shown in the exemplary embodiments.

Figure 5:
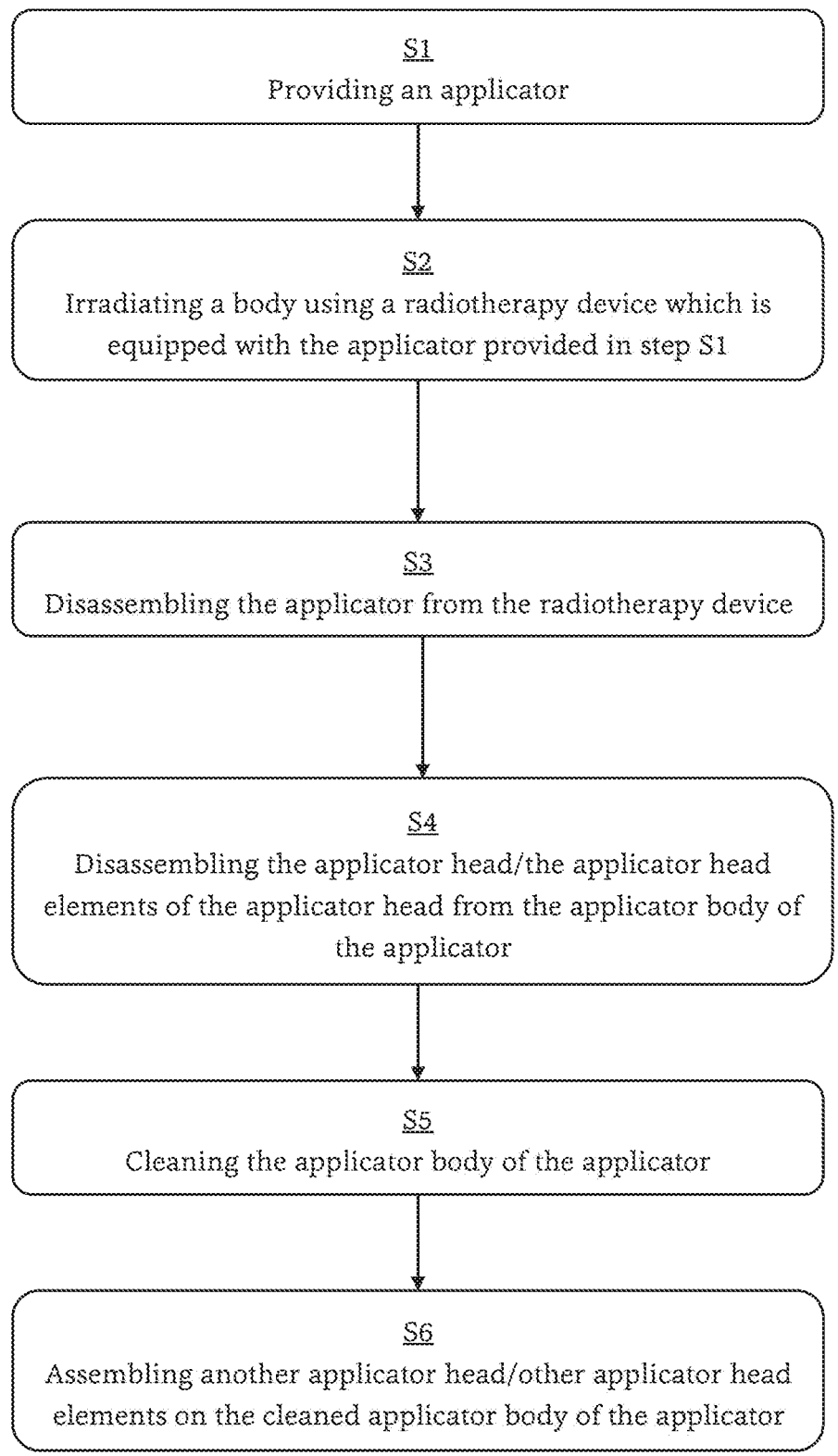
FIG. 5 shows a method for using an applicator according to an exemplary embodiment of the disclosure.

FIG. 5 shows a method for using one of the applicators described herein according to an exemplary embodiment of the disclosure.

An applicator is provided in a first step S1. By way of example, the applicator can be one of the applicators 1, 101, 201, or 301 described above. In the present case, applicators 1 and 301 are taken as representatives for the description.

In a subsequent step S2, a body to be treated is irradiated using the applicator 1 provided in step S1 and a radiotherapy device 3. As illustrated in exemplary fashion in FIG. 1B, the applicator head 13 is assembled on the applicator body 11 to this end and the radiotherapy device 3 is inserted into the applicator 1 via the adapter section 15, and so the situation sketched out in FIG. 1B is obtained. The radiotherapy device 3, to which the applicator 1 has been attached in this way, is now inserted into the body to be treated by therapy, with the applicator head element 13 being at least partly inserted into the body to be treated by therapy. Subsequently, radiation, for example x-ray radiation, is generated at the end 9 by the radiotherapy device 3 and emitted to the body to be treated by therapy by the applicator head 13.

Following the irradiation in step S2, the applicator can be disassembled from the radiotherapy device in step S3, as shown in FIG. 1A.

In a subsequent step S4, the applicator head 13 or the applicator head elements 313A to 313C are disassembled from the applicator body 11 or 311, in each case without damage. In the case of FIGS. 1A and 1B, the applicator head 13 is disassembled from the applicator body 11 by releasing the plug connection between the applicator head 13 and the applicator body 11. In the case of FIG. 4A to 4C, the applicator head elements 313A to 313C are disassembled from the applicator body 311 without damage by virtue of the screw connection between the applicator head elements 313A to 313C being initially released and the interlocking connection between the applicator head elements 313A to 313C and the applicator body 311 being subsequently released.

The applicator body 11 can be cleaned in a subsequent step S5. Consequently, the applicator body 11 can be reused. The applicator body 11 forms the greatest part of the applicator 1 and it is therefore particularly advantageous to use the applicator body 11 multiple times. By contrast, the applicator head or the applicator head elements can be significantly smaller and therefore cheaper than the applicator body. Therefore, the applicator head or the applicator head elements can be used as disposable products, i.e., as products that are only used once.

To prepare a further irradiation, an applicator can be provided as per step S6 by virtue of another applicator head or other applicator head elements being assembled on the cleaned applicator body. Alternatively, the applicator head or the applicator head elements can be cleaned and reassembled on the cleaned applicator body in step S6. In this way, all parts of an applicator can be used repeatedly.

It is understood that the foregoing description is that of the exemplary embodiments of the disclosure and that various changes and modifications may be made thereto without departing from the spirit and scope of the disclosure as defined in the appended claims.

What is claimed is:

1. An applicator for a medical radiotherapy device for carrying out therapy with radiation, the applicator comprising:
   an applicator head; and
   an applicator body,
   wherein the applicator head and the applicator body are embodied such that the applicator head can be assembled on, and disassembled from, the applicator body, in each case without damage, and
   wherein the applicator head comprises at least two separate applicator head elements, which are embodied such that the at least two separate applicator head elements can be assembled on, and disassembled from, one another, in each case without damage.

2. The applicator according to claim 1, wherein the applicator head and the applicator body comprise a first assembling mechanism, which is configured to provide a mechanical connection between the applicator head and the applicator body, and which can be released without damage.

3. The applicator according to claim 2, wherein the first assembling mechanism provides a screw connection, a plug connection, an interlocking connection, a force-fit connection between the applicator head and the applicator body.

4. The applicator according to claim 2, wherein the applicator head elements comprise a second assembling mechanism, which is configured to provide a mechanical connection between the applicator head elements, and which can be released without damage.

5. The applicator according to claim 1, wherein the applicator head elements and the applicator body are embodied such that a mechanical connection between the applicator body and the applicator head elements, which can be released without damage, is established when the applicator head elements are assembled on one another.

6. The applicator according to claim 1, wherein a section of the applicator body is at least in part surrounded by the applicator head when the applicator head is assembled on the applicator body, and
   wherein the section has a spherical external shape or an ellipsoid external shape.

7. The applicator according to claim 1, wherein the applicator head has a spherical external shape or an ellipsoid external shape when the applicator head is assembled on the applicator body.

8. The applicator according to claim 1, wherein the applicator body and the applicator head are made from a same material.

9. The applicator according to claim 1, wherein the applicator head comprises at least two applicator head elements, which have different absorption characteristics in respect of the radiation.

10. An applicator system comprising:
    a plurality of different applicators according to claim 1, and
    wherein the applicator body of all of the plurality of different applicators is the same.

11. The applicator system according to claim 10, wherein the applicators have different sizes and/or shapes when the respective applicator heads are assembled on the applicator body.

12. An applicator for a medical radiotherapy device for carrying out therapy with radiation, the applicator comprising:
    an applicator head; and
    an applicator body,
    wherein the applicator head and the applicator body are embodied such that the applicator head can be assembled on, and disassembled from, the applicator body, in each case without damage,
    wherein a section of the applicator body is at least in part surrounded by the applicator head when the applicator head is assembled on the applicator body, and
    wherein the section has a spherical external shape or an ellipsoid external shape.

13. The applicator according to claim 12, wherein the applicator head and the applicator body comprise a first assembly mechanism, which is configured to provide a mechanical connection between the applicator head and the applicator body, and which can be released without damage.

14. The applicator according to claim 13, wherein the first assembling mechanism provides a screw connection, a plug connection, an interlocking connection, and a force-fit connection between the applicator head and the applicator body.

15. The applicator according to claim 12, wherein the applicator head has a spherical external shape or an ellipsoid external shape when the applicator head is assembled on the applicator body.

16. The applicator according to claim 12, wherein the applicator body and the applicator head are made from a same material.

17. The applicator according to claim 12, wherein the applicator head comprises at least two applicator head elements, which have different absorption characteristics in respect of the radiation.

18. An applicator system comprising:
   a plurality of different applicators according to claim 12, and
   wherein the applicator body of all of the plurality of different applicators is the same.

19. The applicator system according to claim 18, wherein the applicators have different sizes and/or shapes when the respective applicator heads are assembled on the applicator body.

\* \* \* \* \*